United States Patent [19]

Angelchik

[11] 4,352,358

[45] Oct. 5, 1982

[54] APPARATUS FOR EFFECTING ANASTOMOTIC PROCEDURES

[76] Inventor: Jean P. Angelchik, 1728 W. Glendale Ave., Phoenix, Ariz. 85021

[21] Appl. No.: 279,205

[22] Filed: Jun. 30, 1981

Related U.S. Application Data

[63] Continuation of Ser. No. 107,765, Dec. 28, 1979, abandoned.

[51] Int. Cl.³ .............................................. A61B 17/11
[52] U.S. Cl. ................................... 128/334 R; 285/162
[58] Field of Search ............... 128/334 R, 283, 214 R, 128/334 C, 325, 341, 343, 348, 313 R, 127; 3/1.4; 285/162, 194, 200, 260

[56] References Cited

U.S. PATENT DOCUMENTS

| | | | |
|---|---|---|---|
| 2,127,903 | 8/1938 | Bowen | 128/334 R |
| 3,447,533 | 6/1969 | Spicer | 128/283 X |
| 3,480,017 | 11/1969 | Shute | 128/344 |
| 4,142,516 | 3/1979 | Adair | 128/1 R |
| 4,164,045 | 8/1979 | Bokros et al. | 3/1.4 |
| 4,182,339 | 1/1980 | Hardy | 128/334 R |

*Primary Examiner*—Michael H. Thaler
*Attorney, Agent, or Firm*—William H. Drummond

[57] ABSTRACT

Apparatus and method for effecting anastomotic procedures. A deformable annular member has two operative modes, a deformed mode in which the member is shaped to be inserted through an opening in the wall of a hollow body member and a normal mode in which the member is retained within and around the opening. A tubular elastic membrane is attached in one open end to the annular member and extends through the opening to the exterior of the body member. A split ring attached to the other end of the tubular membrane radially tensions the membrane and sealingly engages it with the edges of the opening in the body member.

1 Claim, 10 Drawing Figures

APPARATUS FOR EFFECTING ANASTOMOTIC PROCEDURES

This application is a continuation of my prior application Ser. No. 107,765, filed Dec. 28, 1979, now abandoned.

This invention relates to surgical apparatus and procedures.

More specifically, the invention pertains to apparatus and methods for effecting anastomotic procedures whereby one hollow body member is joined through an opening in its wall to another hollow member.

More particularly, the invention relates to apparatus and procedures which are specially adapted for use in effecting vascular by-pass operations utilizing artificial conduits to by-pass part of the normal circulatory system to increase the blood supply to various parts of the body.

In still another respect the invention pertains to apparatus and procedures useful in performing so called "full anastomosis" where two natural body organs are joined to each other such as, for example, the small intestine and stomach or the ureter and colon.

According to present surgical practice, the implantation of arterial grafts is carried out by placing clamps on the artery, making an incision in the arterial wall by the clamps, and then suturing a by-pass conduit made of dacron, teflon, or the like around the incision. The other end of the conduit is attached by similar procedures to other organs of the body, and the clamps are removed. Within a few hours natural body mechanisms will seal the graft by growing tissue around it to effect a fluid type connection between the graft and the artery. While such operations are routinely performed and have achieved a very high degree of reliability, the possibility always exists that the junction between the transplant and the artery will leak allowing fluid to enter other body cavities causing serious complications. Of course, this possibility is most serious immediately after the transplant has been accomplished and diminishes with the passage of time as the body reacts to seal the connection between the transplant and the artery.

According to other common surgical procedures, various other organs of the body are joined directly together by so called "full anastomosis", a common example of which is the construction of a direct outlet from the stomach into the small intestine by effecting a surgically constructed passage from the interior of the stomach to the interior of the small intestine. Again, this is commonly effected by making an incision in the stomach and the stomach wall and the wall of the small intestine and joinging the peripheries of the two incisions by suturing. Again, such procedures are highly developed, safe and effective but, likewise, the possibility of leakage of the full and "anastomatic joint" always exists prior to the time the body closes the joint by natural tissue growth.

The above described partial and full anastomosis operations require an unusually high degree of skill to safely and effectively perform and, even with the application of such skill, they are not completely foolproof.

Accordingly, it would be highly desirable to provide apparatus and methods for use in effecting full and partial anastomosis in which the possibility of leakage of the joints between the body organs or between a body organ and a transplant is materially reduced, and in which the complexities of the operation are reduced, with significant time savings which themselves yield medical dividends by lessening the traumatic effects of the surgical procedures.

Accordingly, it is a principal object of the present invention to provide improved apparatus and methods for use in effecting anastomotic procedures.

Yet another objective of the invention is to provide such apparatus and methods which unable the surgeon to more conveniently and reliably perform anastomotic procedures.

Still another objective of the invention is to provide such apparatus and methods which enable the surgeon to more quickly effect anastomotic procedures.

These and other, further and more specific objectives and advantages of the invention will be apparent to those skilled in the art from the following detailed description thereof, taken in conjunction with the drawings, in which.

Figure 1:
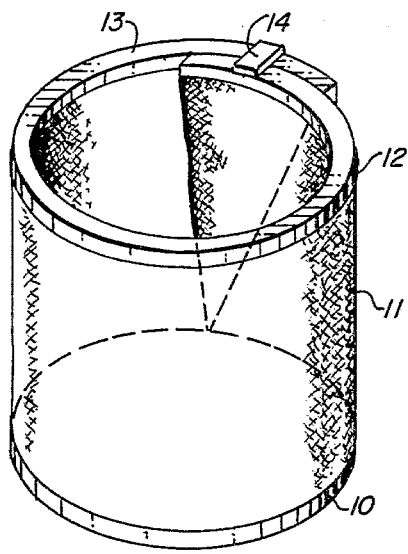
FIG. 1 is a perspective view of a sleeve connector constructed in accordance with and useful in the practice of the invention, showing the connector in its compressed condition just prior to use.

Briefly, in accordance with one embodiment of the invention I provide apparatus for use in effecting anastomotic procedures whereby one hollow body member is joined through an opening in its wall to another body member. The other hollow member may be either a transplant such as a dacron or teflon conduit (a partial anastomosis) or it may be another natural body member (a full anastomosis).

The apparatus comprises a tubular annular member having at least two operative modes, a deformed mode in which the member is shaped to be inserted through an opening in the wall of the hollow body member into the interior thereof, and a normal mode in which the member is shaped to be retained within the body member around the opening therein. One open end of a tubular elastic membrane is attached to the annular member and is dimensioned to extend through the opening to the exterior of the hollow body member. Means are provided for radially tensioning the elastic tube to sealingly engage with the edges of the opening in the body member.

In surgical by-pass operations, this apparatus is used to effect the anastomotic joint by attaching one end of a length of artificial conduit to the deformed annular member before it is inserted through the opening in the hollow body member and the elastic membrane sealingly engages the edges of the opening and prevents loss of blood through the joint until natural tissue seals the joint.

According to another presently preferred embodiment of the invention, I provide a method for effecting anastomotic procedures including the steps of affixing one end of a tubular elastic membrane to a deformed annular member which is shaped and dimensioned when deformed to be inserted through an opening into the body member and is adapted to assume its normal shape after insertion and be retained within the body member around the opening. The annular member is first deformed and then inserted into the opening in the hollow body member with the tubular member extending from the interior to the exterior of the body member. The portion of the member extending through the opening is then radially tensioned to sealingly engage the edges of the opening.

The practice of the invention will be illustrated for those skilled in the art by reference to an arterial graft procedure shown in the drawings.

The presently preferred embodiment of the apparatus of the invention is depicted in FIGS. 1-3a. The apparatus consists of an annular member 10 fabricated from a tubular material such as plastic or the like. The normal shape of the annular member 10 is substantially circular as shown in FIG. 1. A tubular elastic membrane 11 is attached to its lower open end to the annular member 10 by any suitable technique and extends upwardly. The upper open end 12 of the tubular elastic membrane 11 is affixed to a split ring 13 which can be compressed as shown in FIG. 1 to reduce its overall diameter, being temporarily in such compressed condition by means of a latch 14 shown in greater detail in FIG. 2.

Figure 2:
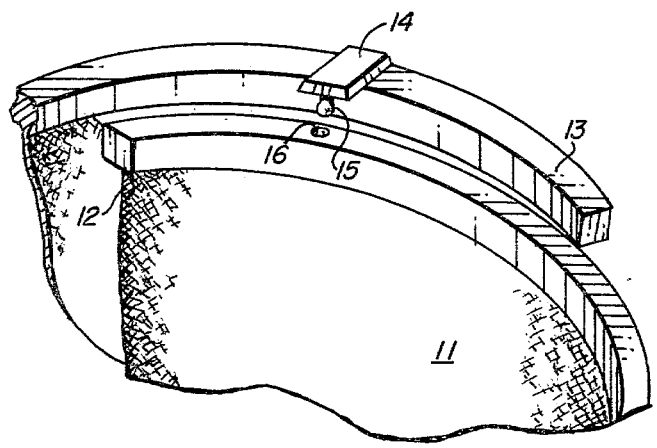
FIG. 2 is a partial sectional view of the connector of FIG. 1 showing details of the latch mechanism which allows the connector to expand and seal the edges of an incision in a hollow body member.

As shown in FIG. 2, the latch 14 is hingedly attached to one portion of the split ring 13 and has a depending projecting 15 which is received in an aperture 16 formed in another portion of the split ring 13 to hold the opened ring 13 in its compressed, reduced diameter condition as shown in FIG. 1.

Figure 3:
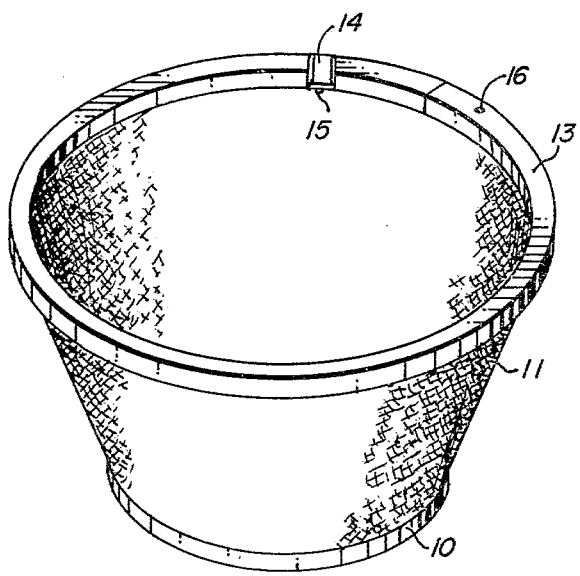
FIGS. 3–3a illustrate the mode of operation of the connector of FIGS. 1–2.
Figure 3A:
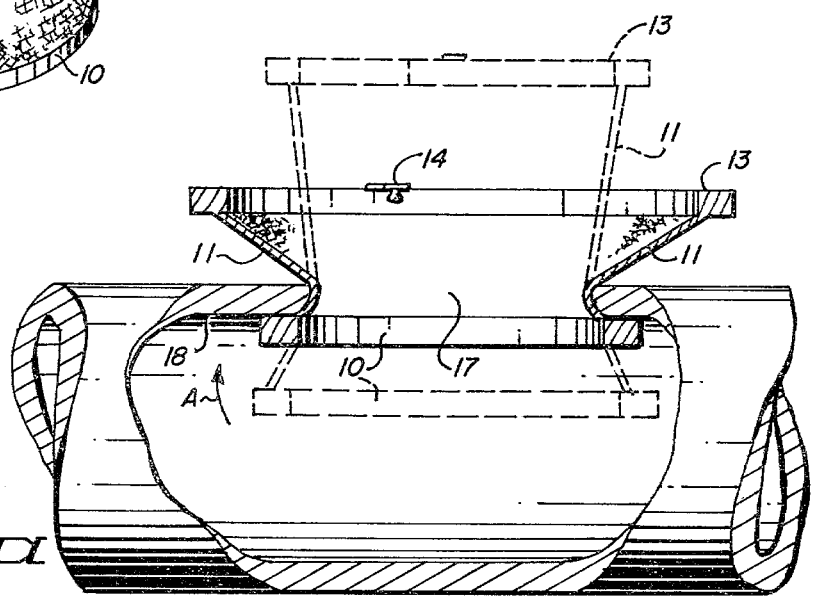

If the latch 14 is merely opened, with no restriction on the movement of the other parts of the connector, allowing the opened ring 13 to expand to its normal diameter, the connector of FIGS. 1 and 2 would assume the configuration shown in FIG. 3 in which the opened ring 13 has opened to its maximum diameter and is connected to the tubular annular member 10 by the tubular elastic membrane 11. If, however, the annular member 10 is inserted through an opening in a hollow body member before releasing the latch 14 of the split ring 13, the connector of FIGS. 1 and 2 will assume the configuration in FIG. 3a. As shown in FIG. 3a, after insertion through the opening 17 in the walls 18 of a hollow body member, the annular member 10 assumes its normal shape around the opening 17, as indicated by the dashed lines. When the latch 14 of the split ring 13 is opened allowing the split ring 13 to expand to its full diameter, the annular member 10 is pulled upwardly in the directon of the arrow A to bear against the lower surface of the wall 18 of the body organ and the expansion of the ring 13 radially tensions the tubular membrane 11 causing the membrane 11 to sealingly engage the edges of opening 17. In this position, the annular member 10 can serve as a firm anchor for a transplant and the membrane 11 temporarily seals the opening 17 against the leakage of blood until natural body tissue seals the joint between the transplant and the wall 18 of the body member.

Use of the connector of FIGS. 1-2 to effect an arterial graft is illustrated in FIGS. 4-9.

Figure 4:
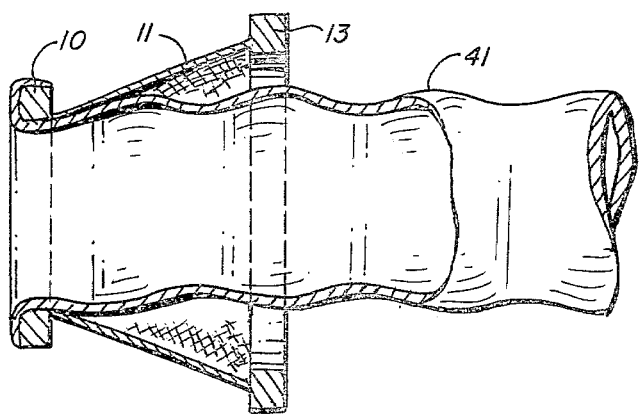
FIGS. 4–9 illustrate various steps of an arterial graft in which the connector of FIGS. 1–2 is employed to graft a synthetic conduit to an artery.
Figure 7:
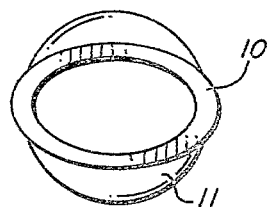
Figure 5:
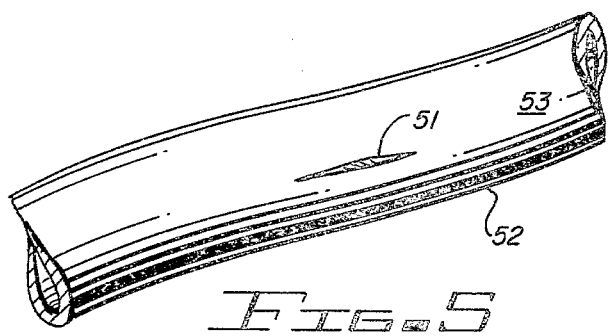
Figure 6:
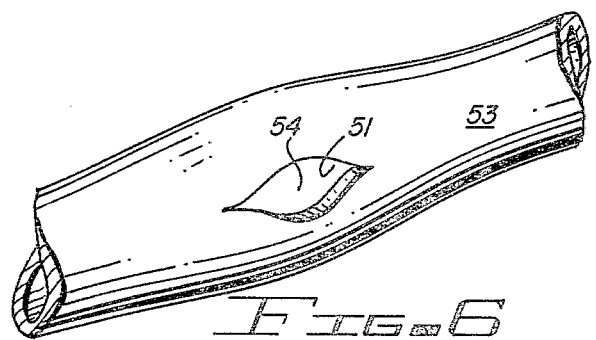

As shown in FIG. 4, before commencement of the surgery, one end of a dacron or teflon tube 41 which will serve as the by-pass conduit is attached by suturing or other suitable technique to the deformable annular member 10 and pass through the expanded ring 13. After placing suitable clamps on the artery 53, an incision 51 is then made as shown in FIG. 5 in the wall 52 of the artery 53, the length of which is smaller than the diameter of the tubular member 10. As shown in FIG. 6, the artery 53 is then compressed towards the incision 51 which opens to form a hole 54. As shown in FIG. 7 the annular member 10 is then compressed to an oval shape which can be inserted through the hole 54 to the interior of the artery 53.

Figure 8:
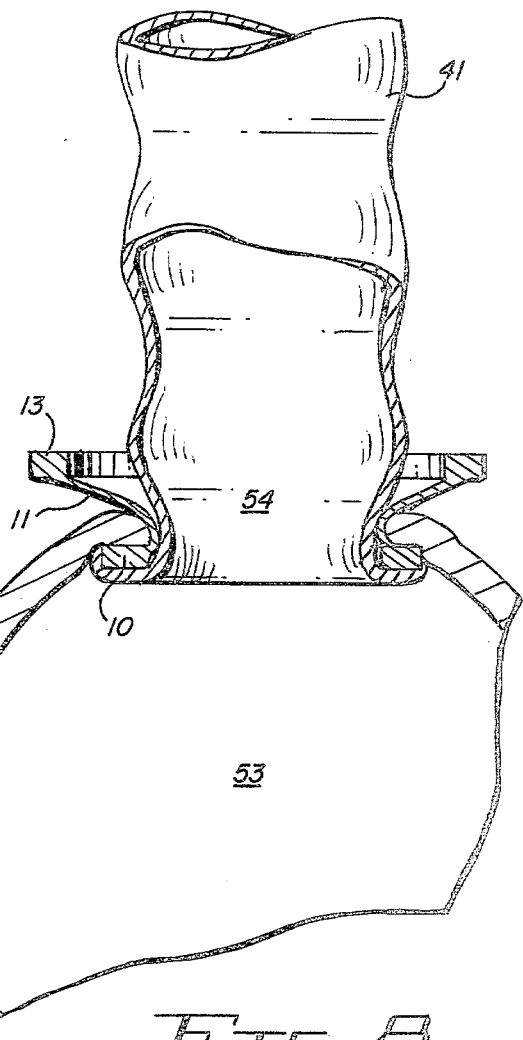

After the deformed annular member 10 is inserted into the oval shaped hole 54 in the artery 53, as shown in FIG. 8, the annular member 10 returns to its normal circular shaped and surrounds the edges of hole 54. The split ring 13 is then expanded by releasing the latch 14 and the expansion of the split ring 13 radially tensions the tubular elastic membrane 11 and sealingly engages the membrane 11 against the edges of the hole 54 in the artery 53. The arterial clamps are then removed.

Figure 9:
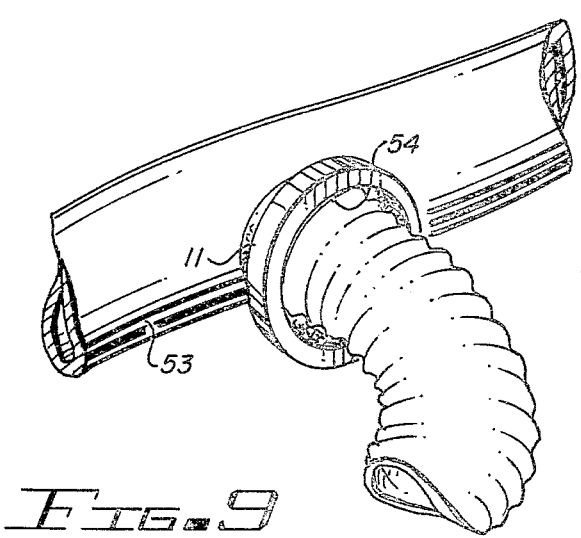

The completed arterial graft is shown in FIG. 9 with the by-pass implant 41 firmly anchored through the hole 54 in the wall of the artery 53 to the tubular annular member 10 located inside the artery 53. The split ring 13 maintains the tubular membrane 11 in sealing engagement with the edges of the hole 54 until the body seals the joint between the artery 53 and the implant 41 with tissue.

If desired, the components of the connector of FIGS. 1-2 can be made of suitable biodegradable material such as polyglycol resins sold under the tradename "Vycril" or "Dexon", such that the components will be degraded and absorbed by the body after the joint is closed by normal body tissue.

As would be appreciated by those of skill in the art, the apparatus shown in FIG. 4 could be utilized as a temporary seal for external body openings formed during operations such as colostomies by merely sealing the free end of member 41 where the free end is the end which is not sutured to member 10.

Having described my invention and the presently preferred embodiments thereof in such terms as to enable those skilled in the art to understand and practice it and having identified the presently preferred embodiments thereof,

I claim:

1. Apparatus for use in effecting anastomotic procedures, to join a first hollow body member at an opening in its wall to a second hollow member and establish fluid communication therebetween, said apparatus comprising:
   (a) a deformable annular member having a generally ring-shaped peripheral portion and a central opening therein and having at least two operative modes, including:
       (i) a deformed mode in which said annular member is shaped to be inserted through the opening in the wall of said first hollow member and be completely received therewithin, and
       (ii) a normal mode in which said annular member is shaped to be retained against the inner surface of said first hollow body member around the opening in the wall thereof;
   (b) a second hollow tubular member having at least one open end, joined at said open end thereof to said annular member and dimensioned, when said annular member is retained with said first hollow body member, to extend from the interior of said first hollow body member, from the central opening in said annular member, to the exterior of said first hollow body member, to provide fluid communication between the interior of said first hollow body member and the interior of said second hollow member;

(c) a liquid-impermeable tubular elastic membrane with an unbroken continuous side wall, disposed concentrically around said second hollow tubular member and having one open end thereof attached to said annular member and dimensioned, when said annular member is retained within said first hollow body member, to extend from said annular member, through said opening in the wall of said first hollow body member, to the exterior of said first hollow body member; and (d) means for radially tensioning said membrane to continuously sealingly engage the edge of the opening in the wall of said first hollow body member completely around the periphery thereof without suturing.

* * * * *